(12) United States Patent
Badali et al.

(10) Patent No.: US 11,947,878 B2
(45) Date of Patent: Apr. 2, 2024

(54) METHOD AND APPARATUS FOR ELECTRON BEAM PROCESSING CONTROL

(71) Applicant: Triple Ring Technologies, Inc., Newark, CA (US)

(72) Inventors: Daniel Salvatore Badali, Ontario (CA); Tobias Funk, Martinez, CA (US)

(73) Assignee: Triple Ring Technologies, Inc.

( * ) Notice: Subject to any disclaimer, the term of this patent is extended or adjusted under 35 U.S.C. 154(b) by 685 days.

(21) Appl. No.: 17/103,857

(22) Filed: Nov. 24, 2020

(65) Prior Publication Data

US 2022/0164489 A1 May 26, 2022

(51) Int. Cl.
| | |
|---|---|
| *G06F 30/20* | (2020.01) |
| *G01T 1/29* | (2006.01) |
| *G06F 3/04815* | (2022.01) |
| *G06F 3/04847* | (2022.01) |
| *G06F 30/12* | (2020.01) |
| *G06F 111/08* | (2020.01) |
| *G06F 111/10* | (2020.01) |

(52) U.S. Cl.
CPC ............... *G06F 30/12* (2020.01); *G01T 1/29* (2013.01); *G06F 3/04815* (2013.01); *G06F 3/04847* (2013.01); *G06F 30/20* (2020.01); *G06F 2111/08* (2020.01); *G06F 2111/10* (2020.01)

(58) Field of Classification Search
CPC .. G06F 30/12; G06F 3/04815; G06F 3/04847; G06F 30/20; G06F 2111/08; G06F 2111/10; G01T 1/29; A61L 2202/24; A61L 2/26; A61L 2/087
See application file for complete search history.

(56) References Cited

U.S. PATENT DOCUMENTS

| | | | |
|---|---|---|---|
| 9,711,325 B2 * | 7/2017 | Boughorbel | H01J 37/28 |
| 2018/0144493 A1 * | 5/2018 | Mulukutla | G06T 17/10 |

FOREIGN PATENT DOCUMENTS

| | | | | | |
|---|---|---|---|---|---|
| CN | 1144015 | A | * | 2/1997 | ............... H05G 1/32 |
| CN | 101120871 | A | * | 2/2008 | |
| CN | 100496386 | C | * | 6/2009 | |
| CN | 101765438 | A | * | 6/2010 | ............ B01D 65/022 |
| CN | 104858430 | A | * | 8/2015 | ............ B22F 3/1241 |
| CN | 106256329 | A | * | 12/2016 | ......... A61F 2/30942 |
| CN | 106462060 | A | * | 2/2017 | ............. H01L 24/81 |
| CN | 109666159 | A | * | 4/2019 | ............... C08J 3/243 |
| EP | 1334031 | B1 | * | 12/2004 | ............. B65B 55/16 |
| EP | 1482305 | A1 | * | 12/2004 | ........... A61B 6/4021 |
| FR | 2987293 | A1 | * | 8/2013 | ............ B21F 10/364 |

* cited by examiner

*Primary Examiner* — Kandasamy Thangavelu

(57) ABSTRACT

A digital representation of an object is formed. The properties of incident electrons are calculated from a parameterized source model and the irradiation of the object is simulated. The particle-matter interactions for a material of the object are calculated. The amount of absorbed dose at locations at the object is calculated. The digital representation of the object is modified in response to an input from a user and the modified digital representation of the object is displayed.

20 Claims, 9 Drawing Sheets

| Application | Typical Energy Range |
|---|---|
| Sterilization | 10 MeV – 12 MeV |
| Food irradiation | 1 MeV – 10 MeV |
| Chain scission and crosslinking | 400 keV – 1 MeV |
| Curing | 70 keV – 300 keV |
| Gemstone coloring | 2 MeV – 25 MeV |
| Power semiconductor processing | 10 MeV – 12 MeV |

FIG. 4

METHOD AND APPARATUS FOR ELECTRON BEAM PROCESSING CONTROL

FIELD

Embodiments according to the present invention relate to electron beam processing control systems. More particularly, embodiments according to the present invention pertain to a method and apparatus for electron beam processing control.

BACKGROUND

Electron beam processing refers to the irradiation of objects with high energy electrons. The incident electrons interact with the material in the object and transfer energy to the object at the location of the interaction. This is quantified in terms of absorbed dose, which is calculated as the amount of absorbed energy per unit mass. The conventional unit of absorbed dose is the kilogray (kGy). The minimum and maximum allowed doses that are delivered to an object are determined by the particular application and appropriate regulations.

Electron beam irradiation is generally characterized by low penetration and high dose rates. Because of this, the density, size, and orientation of the irradiated object must be considered when designing an electron beam processing application.

Electron beam processing is used for a number of applications, the most prominent examples of which are the sterilization of single-use medical devices, the modification of material properties, and the contamination control of consumer products and food. These and other applications are described briefly below.

Sterilization is a regulatory requirement for many medical devices and healthcare products, and exposure to an intense electron beam is one of the most popular forms of sterilization. The dose delivered to the object from the electron beam breaks the DNA chains in living organisms, resulting in microbial death.

The irradiation of food (mainly meat, fruit, vegetables, grains, herbs, and spices) with an electron beam is an effective way to eliminate food-borne pathogens and extend shelf life. Irradiated food is safe to eat, has a negligible impact on the appearance of the food, and only results in a minimal loss of nutritional value (similar to the losses resulting from cooking, canning, or freezing). Similarly, electron beam processing is used in the agriculture industry to eliminate pathogens in animal feed, sterilize growth media and planting pots, and disinfect beehives in the apicultural sector.

Electron beam processing is used to alter the physical properties of materials, most notably by inducing effects such as chain scission and crosslinking in polymer-based materials. Chain scission breaks long polymer chains into smaller units, thus reducing the molecular weight. This allows the degraded material to be ground into finer powders. Crosslinks are chemical bonds that connect adjacent polymer chains together. Crosslinking severely limits molecular motion, which can lead to improvements in the thermal, mechanical, and chemical properties of the material. Crosslinking and chain scission occur at the same time, with the dominant reaction being dictated by the polymer chemistry. Electron beam processing is additionally used for curing (polymerize liquid resins into coatings, inks, or adhesives) and grafting (changing the surface properties of a film by bonding a polymer with a pre-polymer).

There are several other markets in which electron beam processing is applied. Electron beam irradiation is routinely used to modify and enhance the colors of precious gemstones, for example changing the color of topaz from clear to sky blue. Electron beam processing is also used for aging studies for electronic components required to have long lifetimes in environments exposed to radiation, in fields such as space, aviation, and nuclear medicine. Additionally, electron beam irradiation can be used to tailor the switching speeds of many silicon-based power semiconductor devices.

In general, the possible interactions of electrons with the object's medium are elastic scattering, inelastic scattering, and Bremsstrahlung emission. Elastic interactions are those in which the energy of the incident electron is the same before and after the interaction, and inelastic interactions are those in which some of the incident electron's energy is transferred to the object. Each of these interactions are described briefly below:

Elastic scattering is an interaction in which the electron retains its energy but changes direction. The angular deflections of electron trajectories in matter are mainly (but not completely) due to elastic scattering.

Inelastic scattering is the dominant energy loss mechanism for electrons with low and intermediate energies, and results in electronic excitations and ionizations in the object's medium. The ejected electrons from ionization events typically cause subsequent ionization events until the electrons' energy is fully dissipated. Similar to elastic scattering, inelastic scattering causes the incident electron to change direction.

When electrons are decelerated by the strong electromagnetic field of an atomic nucleus, the lost kinetic energy is converted into emitted radiation called Bremsstrahlung radiation.

Most electron beam processing applications use a linear accelerator to produce the required high energy electrons. In the conventional design of such an accelerator, free electrons are produced through thermal emission, photoemission, or field emission and then accelerated to near the speed of light by strong electric fields. The electrons are then focused to a scan horn and scanned by a magnetic lens in one or more dimensions. The object to be scanned then passes through the scanning beam at a fixed speed on a conveyor belt. The most important characteristics of the linear accelerator are the energy of the output electrons (in keV or MeV) and the power (in kW), which need to be tuned for specific processing applications.

For all electron beam processing applications, it is important to ensure that the dose delivered to the object is held constant. This is sometimes achieved by regulating the conveyor belt speed with feedback from the measured electron beam current, and by precisely controlling the beam's current, scan width, and energy. Furthermore, it is desirable to have a uniform distribution of dose throughout the object to ensure homogeneity in the material's properties.

It is currently the standard practice to measure the dose using dosimeters, which are often small pieces of radiochromic film. These dosimeters have a substantial area (for example, 1 cm×1 cm), and so measure the average dose over their extent. This substantial size of the dosimeters limits their ability to measure the dose in small structures, such as the interiors of needles. There is currently no way to measure the dose in such restricted geometries. Furthermore, dosimeters only measure the dose in the location where they are placed; that is, although they allow for spot checks of the dose distribution, they cannot measure the full, three-dimensional dose distribution. An additional limitation of dosimeter measurements is that they can only measure the dose over a limited range. For example, the response of many radiochromic films degrades below five kGy.

Because of the limited ability of dosimeters to characterize the three-dimensional dose distribution, it would be advantageous to provide an alternative method for analyzing the distribution of dose absorbed by an object during electron beam processing.

SUMMARY

The present invention pertains to methods and apparatuses for electron beam processing control. A method uses computer simulations to accurately calculate the three-dimensional distribution of dose absorbed by an object during electron beam processing. The simulation uses a digital representation of the object, which allows the method to be applied without incurring the resources to construct a physical object. The dose distribution is formed by dividing the object and its components into volume elements and tallying the dose absorbed by each volume element. Access to the three-dimensional dose distribution offers insights into the effectiveness of the electron beam processing application that would not otherwise be available; for example, the invention can calculate if the required dose uniformity is required for crosslinking, or if sufficient dose is delivered for sterilization.

The energy, direction, and position of each incident electron in the simulation is calculated from a parameterized model of a typical electron source for electron beam processing applications. An apparatus and method are included to calculate the parameters of the source model by comparing the simulated and measured dose delivered to a structure of a known material.

The invention includes a system to manage the simulations and interface with a user. The system includes a graphical user interface that is used to configure the simulation and to display the digital representation of the object, a "snapshot" of the simulations showing individual particle trajectories, and also the three-dimensional dose distribution.

The invention overcomes the limited ability of dosimeters to characterize the three-dimensional dose distribution, by providing an alternative method for analyzing the distribution of dose absorbed by an object during electron beam processing.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

FIG. 4 is a table listing the typical energy ranges for several electron beam processing applications;

DETAILED DESCRIPTION

Figure 1:
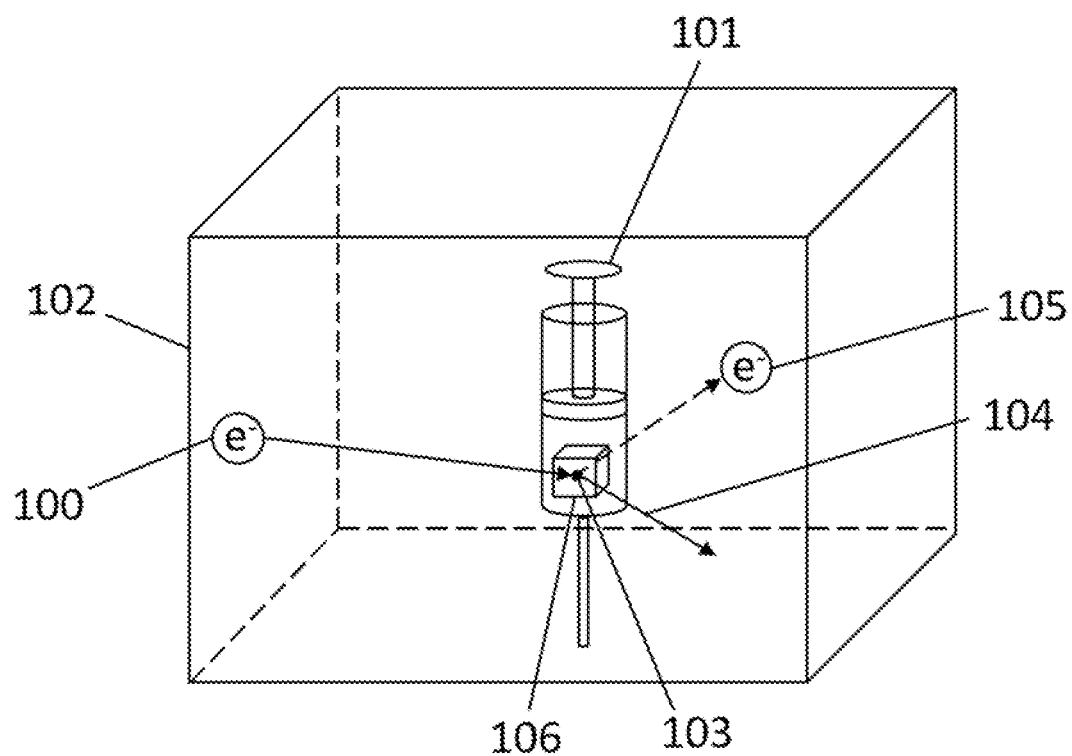
FIG. 1 is a diagram showing the components of a simulation of an electron interacting with an object in accordance with the present disclosure.

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

It will also be understood that the present invention will be described in terms of a given illustrative architecture; however, other architectures, structures, materials, and process features and steps may be varied within the scope of the present invention.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "forming," "simulating," "calculating," "modifying," "displaying," "comparing," "generating," "determining," or the like, refer to actions and processes of an apparatus or computer system or similar electronic computing device or system (e.g., the system of FIG. 9). A computer system or similar electronic computing device manipulates and transforms data represented as physical (electronic) quantities within memories, registers or other such information storage, transmission or display devices.

Some elements or embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM) or dynamic RAMs (DRAMs), read only memory (ROM), electrically erasable programmable ROM (EEPROM), flash memory (e.g., an SSD) or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Because it is impractical to measure the three-dimensional dose delivered to an object during electron beam processing, embodiments according to the present invention use computer simulations to calculate the dose distribution. Such simulations are illustrated in FIG. 1, which shows an electron 100 impinging on an example of an object 101. The simulations take place in a world volume 102 that completely encompasses the entirety of the object 101 and the initial positions of all electrons 100. As the electrons propagate, they undergo interactions 103 that can alter the electrons' trajectories 104. Some interactions also generate secondary particles 105, which may be electrons or particles of a different type. The object 101 is composed of volume elements 106, which are used to spatially locate dose deposited by electron-matter interactions 103.

Figure 2:
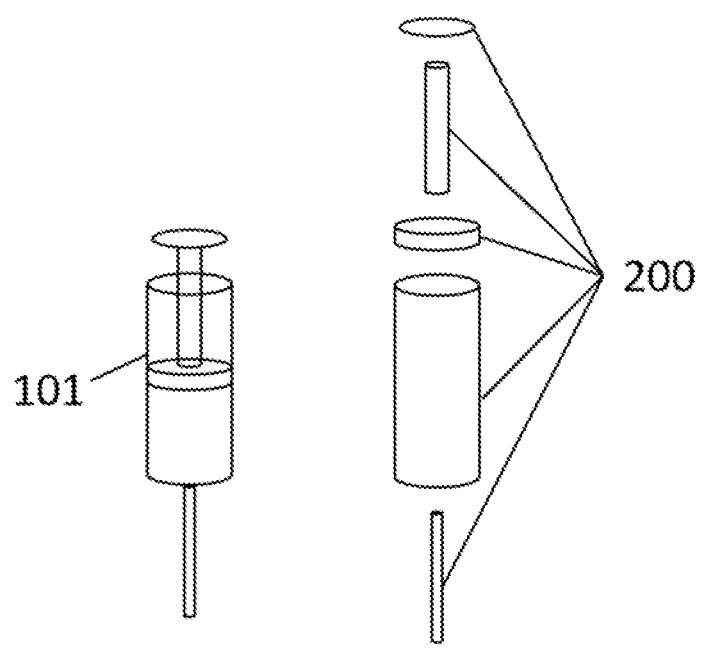
FIG. 2 is a diagram showing a digital representation of an object composed of individual components in accordance with the present disclosure.

The object 101 may be constructed from multiple components 200, as illustrated in FIG. 2. Each component 200 in the object 101 is assigned a single material in the simulation. If the object 101 contains a component that could be composed of multiple materials, then that component can be further broken down into components of a single material. The object 101 may correspond to a digital representation of an actual physical object or may solely exist digitally. This allows users to employ the invention without incurring the expense of physically constructing the object they wish to analyze.

Different embodiments of the invention may use different digital representations of each of the components 200 in the object 101. One possibility is to use constructive solid geometry, where the components are built out of Boolean combinations of simple shapes (spheres, cylinders, cubes, etc.). Another possibility is to use a boundary representation, which represents each component 200 as a set of connected surface elements. These surface elements are typically Non-uniform rational B-splines (NURBS), or a simple surface mesh of connected vertices and edges. Surfaces meshes are typically constructed of triangles or quadrilaterals but can also be unstructured and consisting of groups of higher-order polygons. Finally, the digital representation of the object 101 can be constructed from cubic voxels.

Figure 3:
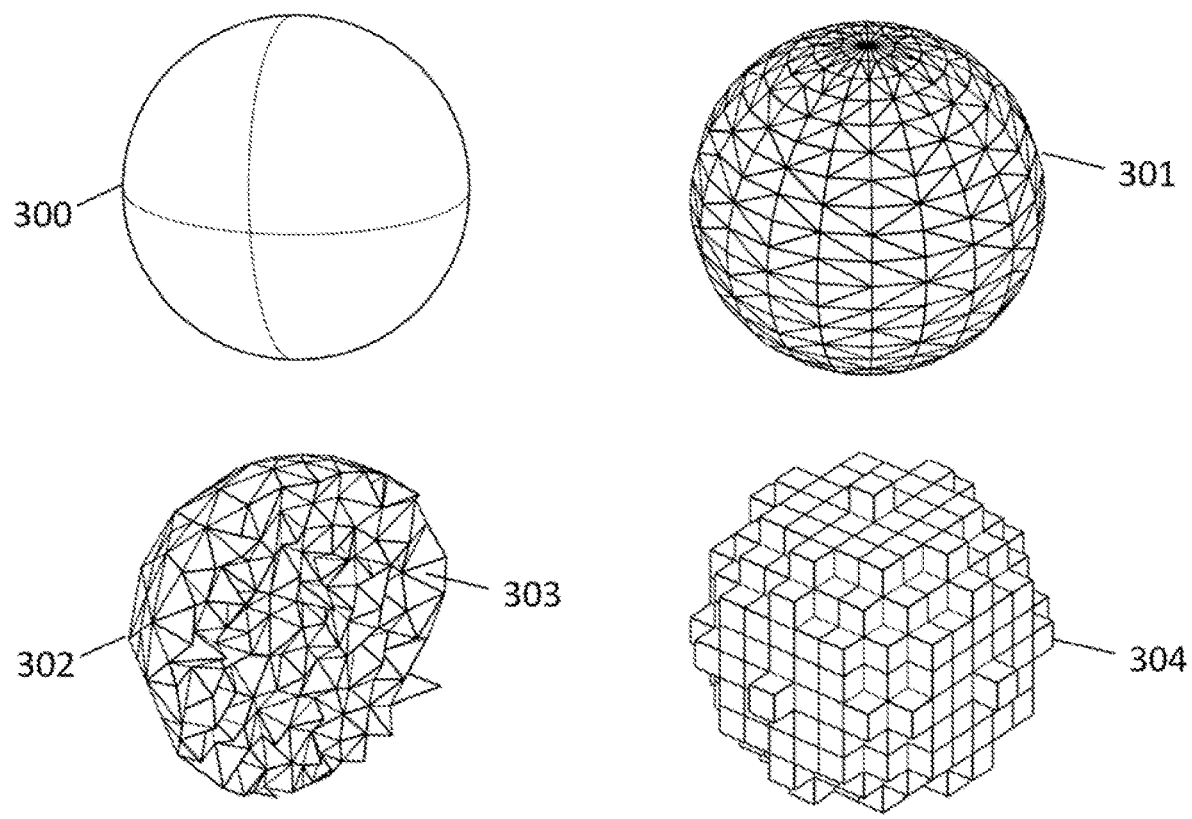
FIG. 3 is a diagram showing different types of digital representations of a sphere in accordance with the present disclosure.

Examples of different digital representations of the object 101 (a sphere in this example) are illustrated in FIG. 3. A sphere is a simple shape, so the constructive solid geometry representation 300 includes only a single sphere. A possible boundary representation is shown constructed from a triangulated surface mesh 301. A second triangulated boundary representation 302 is also shown, with half of the sphere cut away to reveal the internal volume mesh composed of tetrahedral volume elements 303. Finally, the sphere is also shown with a voxelized representation 304.

The invention includes a method to score the three-dimensional spatial distribution of dose absorbed throughout the object 101, as calculated by the simulation. In particular, the simulation world volume 102 is divided into volume elements, each of which is assigned a single material. In some embodiments of the invention, the entire world volume 102 is filled with volume elements, whereas in other embodiments, only parts of the entire world volume 102 (for example, only the object 101) are composed of volume elements. The object 101 may be composed of multiple volume elements. The boundaries of the volume elements may coincide with the boundaries of the object's components, or the volume elements may contain the boundaries of the object's components. The latter occurs, for example, when the volume elements are cubic voxels and so do not necessarily align with the boundaries that define the object's components. During the simulation, the location of each inelastic interaction that results in energy being deposited into the object 101 is used to identify in which volume element the interaction occurred. The energy deposited by each inelastic event is tallied to calculate the total energy deposited into each volume element. Because the volume element has an established material and volume, the total deposited energy is converted into the total deposited dose.

In some embodiments of the invention, each component 200 of the object 101 is represented by a single volume element of a polyhedral surface mesh. Such meshes may be constructed from either triangles or quadrilaterals. With this type of meshing, each component 200 of the object 101 can be assigned a single volume for the total dose it absorbed during a simulation run. Therefore, the granularity of the resulting three-dimensional distribution of dose is limited by the sizes of the components in the object 101.

In other embodiments of the invention, each component 200 of the object 101 is composed of multiple volume elements, which combine to fill the component's volume. A particular example is the three-dimensional meshing of the component's volume with polygonal elements. These polygons are commonly tetrahedrons, although pyramids, triangular prisms, and hexahedrons are also possible. In an embodiment, all polygonal elements of a component have the same material. Using polygonal meshes avoids the partial volume effects that are present when using a voxelized volume (e.g., a mesh with cubic elements) to score dose. Furthermore, this type of volume meshing allows the three-dimensional distribution of dose to be sampled with a fine resolution, limited by the polygonal element's size. Because each polygonal volume element will be assigned its own absorbed dose value at the end of each simulation run, the set of volume elements that constitute a single component in the object 101 can be used to approximate the three-dimensional distribution of dose within the component.

Physical models most important to electron transport in matter have been considered and employed. Processing with electron beams gives certain constraints that permit ignoring physics not relevant to the problem at hand. In particular, electron beam processing facilities generally use electrons strictly less than 100 MeV (typical energy ranges are tabulated in FIG. 4). At these low energies, the following electron-matter interactions can be modeled by the invention:

Møller scattering of the incident electrons from atomic electrons;
Bremsstrahlung photon created by acceleration of the incident electrons in the nuclear and atomic electric fields;
Elastic scattering of the incident electrons and positrons from nuclei; and
Excitation of atoms by the incident electrons.

Furthermore, the interactions of photons with matter (e.g., Compton scattering, Rayleigh scattering, photoelectric absorption, and pair production) and positrons with matter (e.g., Bhabha scattering from atomic electrons, annihilation with atomic electrons, elastic scattering from nuclei, and atomic excitations) can be modelled. Other statistically less likely photon interactions such as triplet production, the double-Compton effect, nuclear Thompson scattering (elastic scattering from the nucleus), and Delbruck scattering (elastic scattering from the Coulomb field of the nucleus) can be ignored in most cases.

Additionally, the interactions between electrons within the beam (so-called space-charge effects) can be neglected. This means that the trajectory of each electron can be considered independently from all other electrons in the electron beam, allowing certain embodiments of the invention to simulate the incident electrons in parallel, when such an implementation is supported by the available hardware. Other implementations may simulate each electron sequentially.

Some embodiments of the invention use a subset of particle types (for example, only electrons, or only electrons and photons), whereas others will account for electrons, positrons, and photons. Similarly, certain embodiments of the invention account for a subset of the possible particle-matter interactions, whereas others use all of those listed above.

Because charged, relativistic particles undergo hundreds of thousands of interactions in a material before slowing down, it is computationally prohibitive to simulate each interaction in the particle's history. As such, the invention employs a condensed history technique, in which many small-effect interactions are combined into a single large-effect interaction. This approximation is valid because most electron interactions involve minimal energy loss and small angular deflections.

The simplest form of the condensed history technique is the Continuous Slowing Down Approximation (CSDA), which is employed in certain embodiments of the invention. With the CSDA, no secondary particles are considered (that is, the simulation only includes electrons but not photons or positrons), and the electrons lose energy according to the material's stopping power. Angular deflections are calculated by considering the average deflection due to multiple consecutive scattering events. Although less accurate, this embodiment of the invention allows for more rapid simulations.

In general, the simulation methodology used by this invention contains the following steps:
1. Use a model of the electron beam source to generate the initial energy, direction, and position of all electrons to be simulated.
2. Transport the electrons through the object, accounting for the appropriate interactions and geometry.

Figure 5:
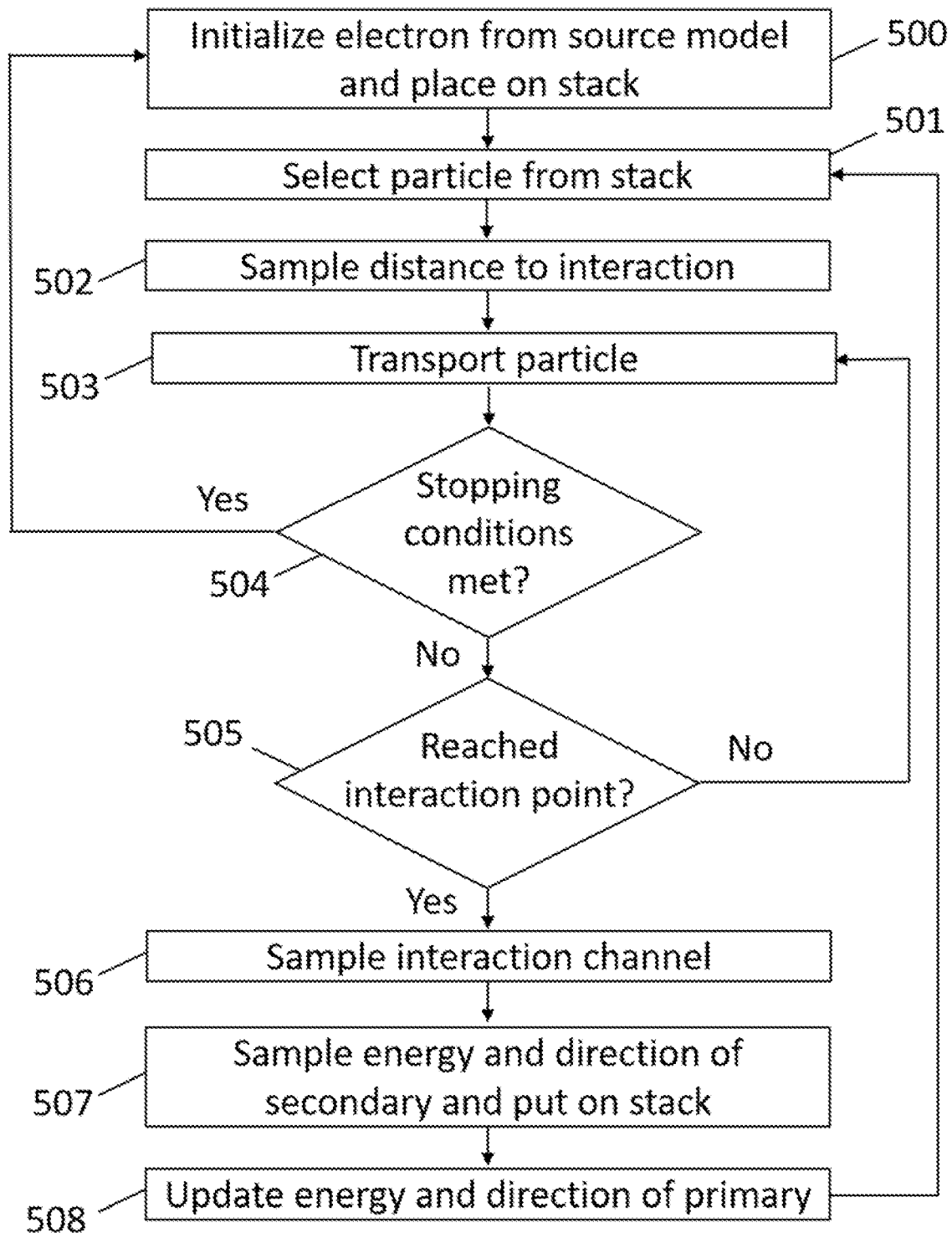
FIG. 5 is a block/flow diagram showing an example of a Monte Carlo algorithm that can be used to simulate the interaction of electrons with an object in accordance with the present disclosure.

FIG. 5 is a flowchart of an implementation of the simulation process that is included in some embodiments of the invention. All or some of the operations represented by the blocks in FIG. 5 can be implemented as computer-executable instructions residing on some form of non-transitory computer-readable storage medium, and executed by a computer system such as the system 900 of FIG. 9.

In embodiments, the process is a Class II algorithm, which correlates primary and secondary particles by combining the condensed history technique with discrete interactions. In particular, bremsstrahlung interactions that result in the creation of photons above a specific energy threshold, and Møller interactions that produce secondary electrons above a specific energy threshold, are treated discretely. All processes below the specified thresholds are accounted for by the CSDA model. For photons, all interactions are treated equally. This implementation only accounts for photons and electrons.

The process illustrated in FIG. 5 makes use of a "stack," which is an array containing the initial energy, direction, and position (collectively known as the "phase space") of all particles (primaries and secondaries) waiting to be simulated. The step 500 of the process is to use the parameterized source model to calculate the initial phase space of the first incident electron and place it on the stack. Some implementations may calculate this initial phase space "on the fly" as each electron is simulated (as shown in FIG. 5), whereas others may calculate the phase space for all electrons to be simulated and then populate the stack before the simulation commences. The phase space of the next particle to be simulated is then selected from the top of the stack (block 501), and the distance to the next interaction is calculated based on the particle's current energy (block 502). In the case of electrons, this refers to the discrete interactions.

Figure 6:
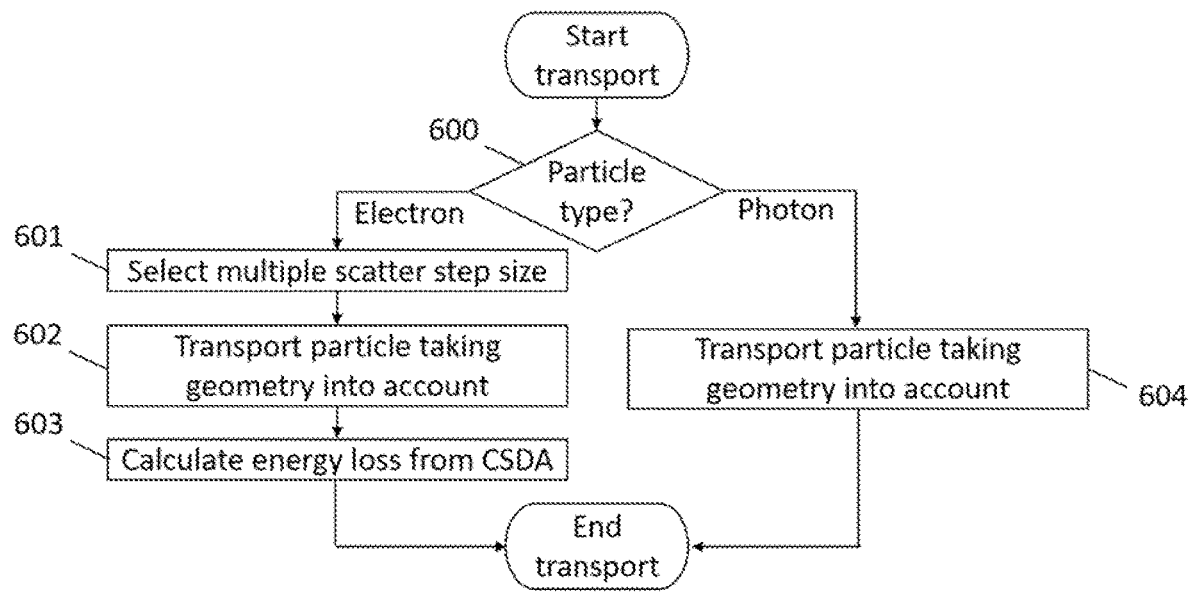
FIG. 6 is a block/flow diagram showing the transport step of the Monte Carlo algorithm shown in FIG. 5.

The particle is then transported (block 503), accounting for the constraints of the geometry. This transportation step (block 503) is different for electrons and photons and is illustrated in FIG. 6 and discussed below. After transporting the particles, it is then checked in block 504 if the particle meets any of the stopping conditions. The stopping conditions in block 504 include, but are not limited to, the following:
1. Is the energy below a specified cutoff energy?
2. Has the electron exited the world volume 102?
3. Has the maximum number of allowed steps been reached?

If one of the stopping conditions is met then the particle is discarded, and the next particle is selected from the stack (block 501). If the particle does not stop but has not yet reached the point of interaction (block 505), then a new transport step is performed. Once the distance to an interaction has been reached (block 505), the type of interaction (e.g., bremsstrahlung or Møller scattering for electrons) is selected (block 506). Secondary particles produced by the interaction (photons for bremsstrahlung and electrons for Møller scattering and photoelectric absorption) are then placed on the stack (block 507), and the energy and direction of the primary particle is updated accordingly (block 508).

Throughout the simulation, as inelastic events occur (either discretely or continuously), the location of the event is used to identify in which volume element the energy was deposited. The simulation includes a tally for each volume element that accumulates the absorbed dose.

The transport step (block 503 in FIG. 5) is illustrated in FIG. 6. All or some of the operations represented by the blocks in FIG. 6 can be implemented as computer-executable instructions residing on some form of non-transitory computer-readable storage medium, and executed by a computer system such as the system 900 of FIG. 9.

Photons and electrons are transported differently (block 600). For electrons, the transport step size is determined from CSDA multiple scattering theory. The electron is then transported (block 602) along its current direction with the determined step size, with the caveat that the step is terminated at any boundary of one of the object's components. Thus, transporting the particle involves accounting for the constraints of the geometry. Specifically, block 602 includes a method to determine whether or not the particle's step will cross the boundary of one of the object's components. For embodiments that use constructive solid geometry, this is relatively easy since the intersection point between the particle's trajectory and the simple shape can be calculated analytically. For embodiments that use boundary representations, the collection of surface elements that define each component's surface can be stored in a bounding volume hierarchy. Such a data structure dramatically reduces the number of surface elements that need to be checked for intersection during the transport of particles. After the transport step (block 602), the continuous energy loss calculated from the CSDA is deducted (block 603). For photons, the transport step is considerably simpler, with the step size equal to the distance to the next interaction point. The actual transportation of the photons (block 604) is identical to that of the electrons, and accounts for the object's geometry.

As mentioned in FIG. 5, the present invention includes a parameterized source model which is used to calculate the phase space of the incident electrons. In electron beam processing applications, the high energy electrons are typically produced from a linear accelerator. However, other particle accelerator types (including, but not limited to, electrostatic particle accelerators, magnetic induction accelerators (e.g., betatrons), and circular accelerators (e.g. synchrotrons)) can also be used. Regardless of the type of accelerator, each electron produced is characterized by an energy, position, and direction in the simulation.

Figure 7:
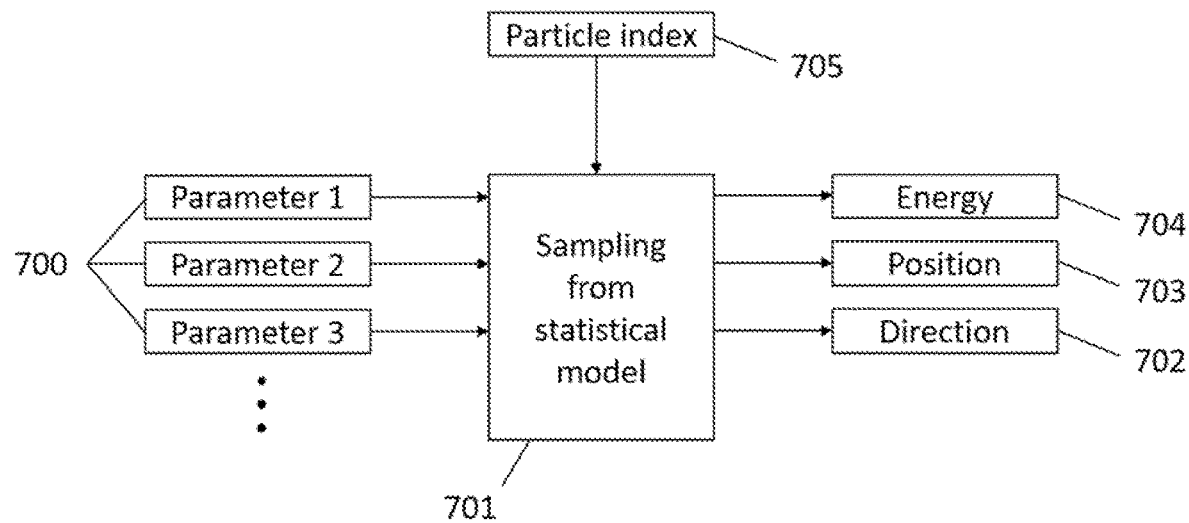
FIG. 7 is block/flow diagram showing the method for calculating the characteristics of the incident electrons from a parameterized source model.

The source model included in this invention consists of a method which takes multiple parameters as inputs, and outputs the phase space of the incident electrons. This is illustrated in FIG. 7. The method uses the input parameters 700 to configure a statistical model 701 that is used to calculate the output direction 702, position 703, and energy 704 of the incident electrons. The direction 702 and position 703 are both three-dimensional vectors, whereas the energy 704 is a single value. Thus, each electron's phase space can be characterized by seven parameters. In an embodiment, a floating-point number is used to represent the phase space, although other numerical representations can be employed.

Different embodiments of the invention may have different numbers of input parameters 700, and some may not have any input parameters 700. The input parameters 700 can have any data type, including, but not limited to, numeric data such as integers and floating-point numbers, Boolean flags, and strings of characters. They can also be arrays (e.g., an ordered sequence) of values of any single data type, or more abstract data types such as associative arrays (e.g., dictionaries or maps). In different embodiments of the invention, all the parameters 700 may all have different data types, or all have the same data type, or only some parameters 700 might have the same data types.

The statistical model 701 may also depend on the particle index 705 as part of its configuration. The particle index 705 is a unique identifying index (e.g., an integer) that is assigned to each incident electron in the simulation. The input parameters 700 may be the same for each simulated incident electron or may depend on the particle index 705.

The statistical model 701 included in the source model of this invention includes a parameterized representation of the initial phase space distribution, which is then statistically sampled to produce the initial phase space for each incident electron. In some embodiments of the invention, the distribution of some of the phase space components may be dependent on each other; that is, there may be a correlation between the electron's position 703 and direction 702, for example. In some embodiments, all of the phase space parameters may be correlated, whereas in others only a subset of the phase space parameters may be correlated. Furthermore, in other embodiments, the energy 704, the position 703, and the direction 702 are each described by an independent distribution. The statistical distributions may be described by mathematical expressions composed of elementary functions, integral equations, or differential equations. Such expressions may be evaluated directly or may require numerical methods. Other statistical models 701 may have distributions defined by look-up tables.

In embodiments, the input parameters 700 are used to configure the distributions used by the statistical model 701. Some of the parameters 700 might be used to configure the distributions for multiple phase space components, whereas others might only be used to configure a single statistical distribution. Some embodiments of the invention might use the input parameters 700 to choose between multiple statistical models 701 for the same phase space components.

Figure 8:
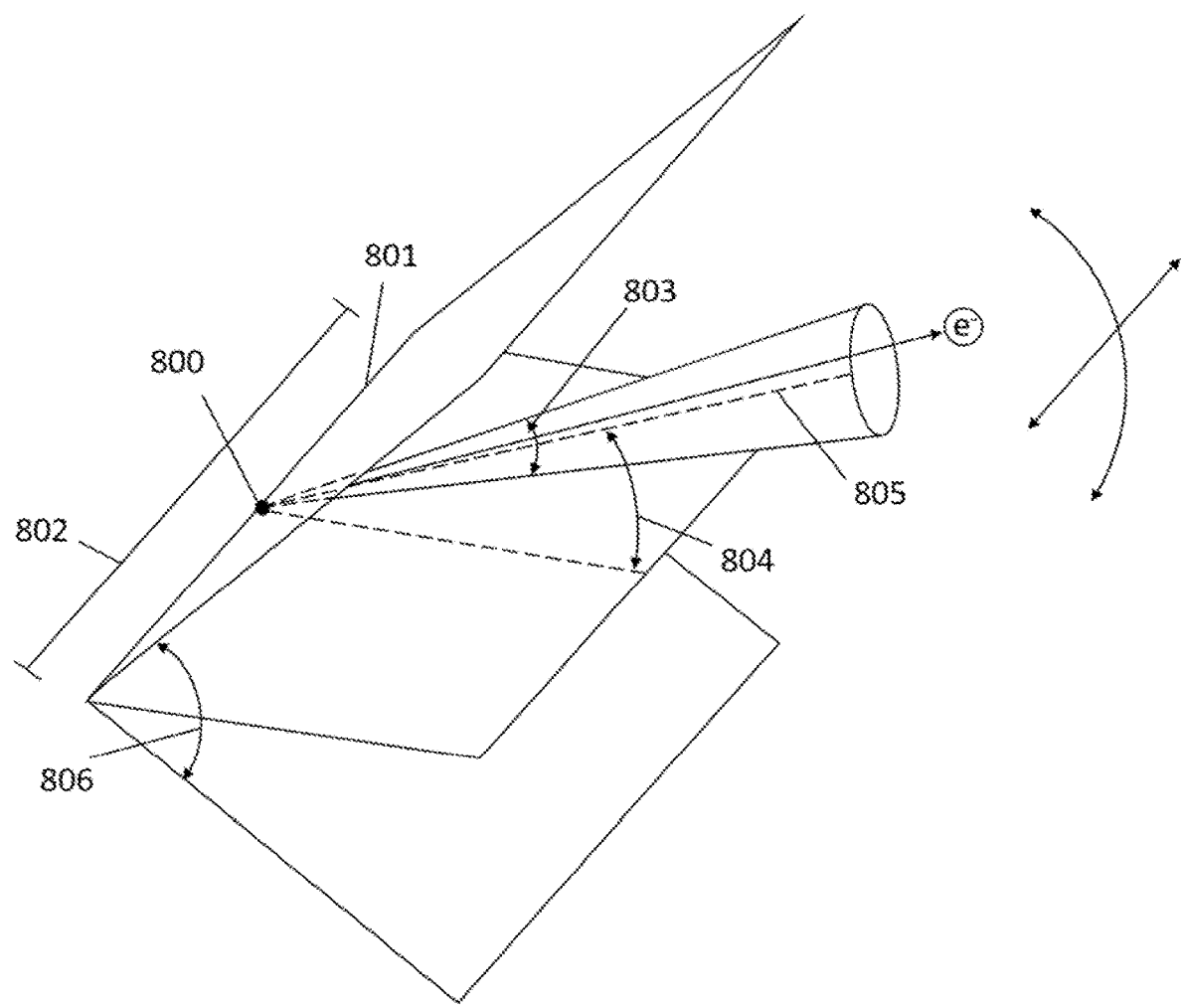
FIG. 8 is a diagram that illustrates the geometry of the parameterized source model in accordance with an embodiment.

FIG. 8 illustrates an embodiment of the source model. This source model approximates the situation in which the objects are moving past the exit horn of a linear accelerator at a uniform speed. This is represented by each electron's initial position 800 randomly being chosen uniformly along a line 801 with a width 802 specified from one of the input parameters. To represent a diverging beam produced from the linear accelerator, the initial direction of each electron is generated uniformly within a cone with a specified full cone angle 803. To represent the electron beam scanning in a sweeping pattern from the accelerator's scan horn, the angle 804 of the cone's axis 805 is uniformly generated in a plane perpendicular to the line 801 containing the initial positions. The axis angle 805 is limited to a fixed range 806, which is configured by one of the input parameters. In this source model, the energy distribution is independent of the distributions of the positions and directions and is defined by a Gaussian distribution. This distribution is described by two parameters: the average initial energy and standard deviation of the distribution.

Other embodiments may use a uniform distribution in a plane for the distribution of initial positions. In an embodiment, the direction is a constant to represent a parallel beam.

In embodiments, the invention includes an apparatus that can be used to experimentally measure the parameters of the source model for a specific electron beam source. This apparatus includes a structure (e.g., a phantom) composed of a known material that, in embodiments, is irradiated by the electron beam in the same manner as the objects to be processed. The structure contains designated spots on which dosimeters are to be placed to measure the dose. The dose measured at these designated locations can be compared against the dose calculated by the simulations, and the difference between the two values can be used to tune the parameters of the source model until a specified agreement threshold is reached. Although there are limitations to dosimeter measurements (as described above), dosimeters can still accurately measure the dose if these limitations are accounted for. To accomplish this, I dosimeters may not be placed in regions expected to have large dose gradients (since the extent of the dosimeter would be insufficient to spatially resolve the gradient), and it needs to be ensured that the minimum dose absorbed by the dosimeters is above the dosimeter's dose sensitivity threshold. Once the measured dose has been reproduced by the source model, then the simulations have been validated and it is reasonable to assume that they accurately predict the true dose distribution delivered to an object during electron beam processing.

Figure 9:
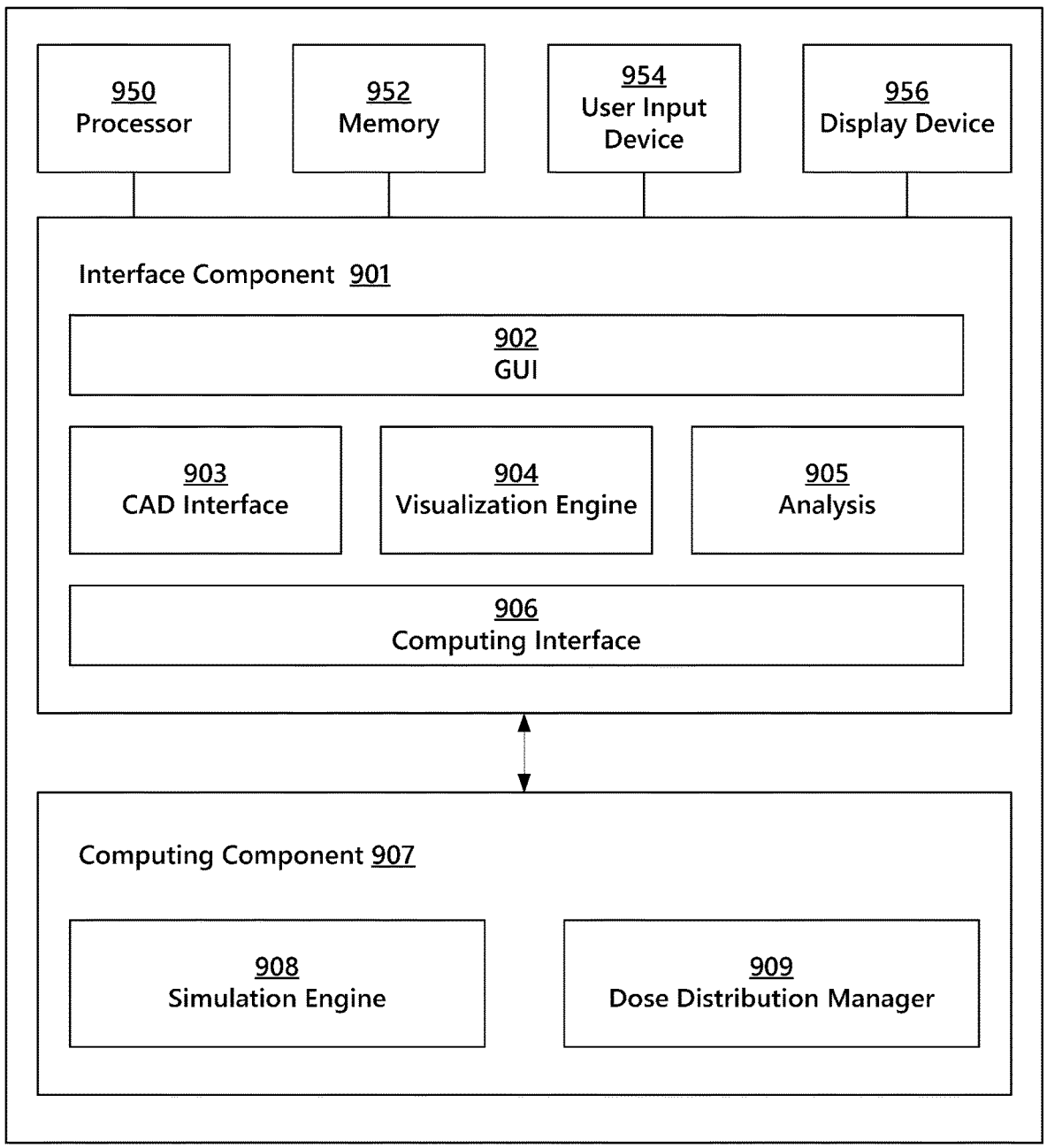
FIG. 9 is block diagram showing the architecture of an illustrative electron beam processing control system in accordance with embodiments of the present invention.

FIG. 9 illustrates an exemplary system 900 for electron beam processing control that can be used to perform the methods of FIGS. 5 and 6, for example. In its most basic configuration, the system 900 includes at least one processing unit 950 and memory 952. The system 900 may also have additional features and/or functionality. For example, the system 900 may also include additional storage (removable and/or non-removable) including, but not limited to, magnetic or optical disks or tape. The system 900 may also contain communications connection(s) that allow the device to communicate with other devices, e.g., in a networked environment using logical connections to one or more remote computers. The system 900 may also include input device(s) 954 such as keyboard, mouse, pen, voice input device, touch input device, etc. Output device(s) 956 such as a display device (e.g., a computer screen), speakers, printer, etc., may also be included.

The system 900 executes an interface component 901 and a computing component 907. The interface component 901 allows the user to interact with a graphical user interface (GUI) 902. In some embodiments of the invention, the interface component 901 is a computer application, whereas in others it is a web user interface, that is, an application accessed via a web browser. Further still, in other embodiments, the interface component 901 is a module of a third-party Computer Aided Design (CAD) software such as AutoCAD®, SolidWorks, Solid Edge, or PTC Creo. The GUI 902 allows the user to configure the electron beam processing simulation and analysis. This includes a CAD interface 903 that allows the user to upload a CAD model that serves as a digital representation of the object 101 (FIG. 1). Commonly used CAD file formats are supported, such as STEP, STL, and IGES. Configuring the simulation includes, but is not limited to, specifying parameters such as the number of electrons to simulate, the coarseness of the volume element meshing to use, and the cutoff energy.

The GUI 902 also interfaces with a visualization engine 904 to display information to the user. In particular, this involves a mechanism to display the CAD object, as well as the three-dimensional distribution of dose. The display of the dose distribution may be mapped to the visualization of the CAD object, which, in some embodiments of the invention, involves coloring each volume element 106 of the object 101 with a color that scales with the total absorbed dose received by that volume element 106 during the simulation. The GUI 902 also provides a way for the user to specify the parameters 700 required by the source model, as well as general parameters to configure the simulation.

The GUI 902 may also include an analysis module 905 for the user to analyze the simulation output. This analysis module 905 calculates statistics on the simulated three-dimensional dose distribution, such as the average dose, the minimum dose, the maximum dose, and the dose uniformity ratio. This information may be displayed graphically or textually to the user. The analysis module 905 allows the user to specify a dose threshold or dose range for each component 200 (FIG. 2) of the object 101. The user is able to define a condition by specifying whether or not they are interested if the absorbed dose is above or below the threshold for each component, or inside or outside of the dose range. In another embodiment of the invention, the software automatically assigns dose thresholds/ranges based on material properties retrieved from a database. The analysis module 905 then determines if each component meets the failure condition and provides a method to communicate this information with the user. This may be done visually, for example, by displaying all components that failed the condition with a specific color and all components that passed the condition with a different color. Alternatively, this information can be displayed textually, for example by displaying a list of all components that failed the condition.

This functionality allows the user to analyze the simulations with respect to the electron beam processing application of interest. For instance, medical devices may contain radiation-sensitive components such as electronics and optics, and so the user might be interested in determining if these components will receive radiation damage during electron beam sterilization. Alternatively, the user may identify which components are required to be sterile, and then use the analysis module 905 to indicate if the dose absorbed by these components is in the range required to sterilize them. As another example, different regimes of polymer crosslinking occur above certain dose thresholds, and so the user might be interested in identifying which components are in which crosslinking regime.

For objects with radiation-sensitive components such as electronics, a shield may be attached to the object to protect the sensitive components, while still allowing components that are required to be sterile to absorb the appropriate dose. Such shields can be composed of materials that strongly attenuate electrons and radiation (e.g., plastic on top of lead), and can be shaped in a way to form barriers between the incident electron beam and the radiation-sensitive components and leave the components to be sterilized unblocked. In some embodiments of the invention, the analysis module 905 includes a method to calculate the ideal shield shape based on the conditions identified by the user for certain components in the object 101. For example, based on knowing which components are required to be sterile and which components are sensitive to radiation, the analysis module 905 can calculate a shield with the appropriate shape. If the user specifies a material and thickness for the shield, the analysis module 905 can be used to perform an additional simulation to calculate the dose distribution in the presence of the shield.

The main software application on the interface component 901 is responsible for parsing and interpreting the configuration parameters and data specified through the GUI 902. This includes the formatting of the volume elements from the digital representation of the object 101. This information is then relayed to a computing component 907 through an interface 906, which manages transferring and receiving data from the computing component 907. This data includes the digital representation of the object 101 (e.g., the list of tetrahedron vertices), the simulation configuration, and the output of the simulation (the simulated dose distribution).

The computing component 907 is responsible for running the simulation through the simulation engine 908. The simulation engine 908 simulates the amount (e.g., energy distribution, number of electrons, current, flux) of the electron beam at locations on the exterior surface of or an interior surface of the object 101. In certain embodiments of the invention, the simulation engine 908 makes use of a Monte Carlo technique, although in general any type of simulation method can be used. The computing component 907 also manages a dose distribution manager 909, which interfaces with the simulation engine 908 and is responsible for scoring the three-dimensional dose distribution and registering it with the digital representation of the object. The dose distribution manager 909 can calculate electron-matter interactions for a material of the object 101, and can calculate an amount of dose deposited at the locations outside or inside the object.

In some embodiments of the invention, the computing component 907 is implemented on a computer system available over the internet (the "cloud"). Such a cloud resource may be managed by a third-party service such as Amazon Web Services, Google Cloud Platform, or Microsoft® Azure. In other embodiments, the computing component 907 will be the same as the interface component 901; that is, the computing component 907 and the interface component 901 may be integrated as a single component. In all cases, the computing component 907 will have access to enough memory to run the simulation and store its inputs and outputs.

Because each particle is simulated independently (see FIG. 5), the simulations fall under the category of "embarrassingly parallel," making them a candidate for utilizing a parallel computing framework such as Graphical Processing Units (GPUs) or multi-threaded central processing units (CPUs). Running the simulations in parallel can dramatically decrease the simulation time compared to a sequential implementation. In particular, some embodiments of the invention use the CUDA® framework with NVIDIA® GPUs. In any case, the computing component 907 has access to the appropriate parallel-computing hardware. Furthermore, the computing component 907 may have multiple CPUs or GPUs over which it can distribute the simulation.

In certain embodiments of the invention, simulations can be run directly on the interface component 901. One purpose of these simulations is to determine and display the trajectories of each individual electron through the GUI 902. Because the calculation of each individual trajectory is slow (since an electron may undergo hundreds of interactions), and because the computing resources of the interface component 901 may be inferior to those of the computing component 907, this simulation may be limited in the number of electrons it will be able to simulate. For example, this simulation may only run 100 incident electrons. Additionally, to further speed up the simulation time, the object may be approximated by a simpler digital representation. For boundary representations, this involves limiting the number of surface elements used to define the object and its components. This simulation may or may not include the calculation and displaying of the three-dimensional dose distribution. Displaying the trajectories calculated in these simulations may involve using different colors for each particle type, and special markers to identify the location and type of each interaction.

Figure 10:
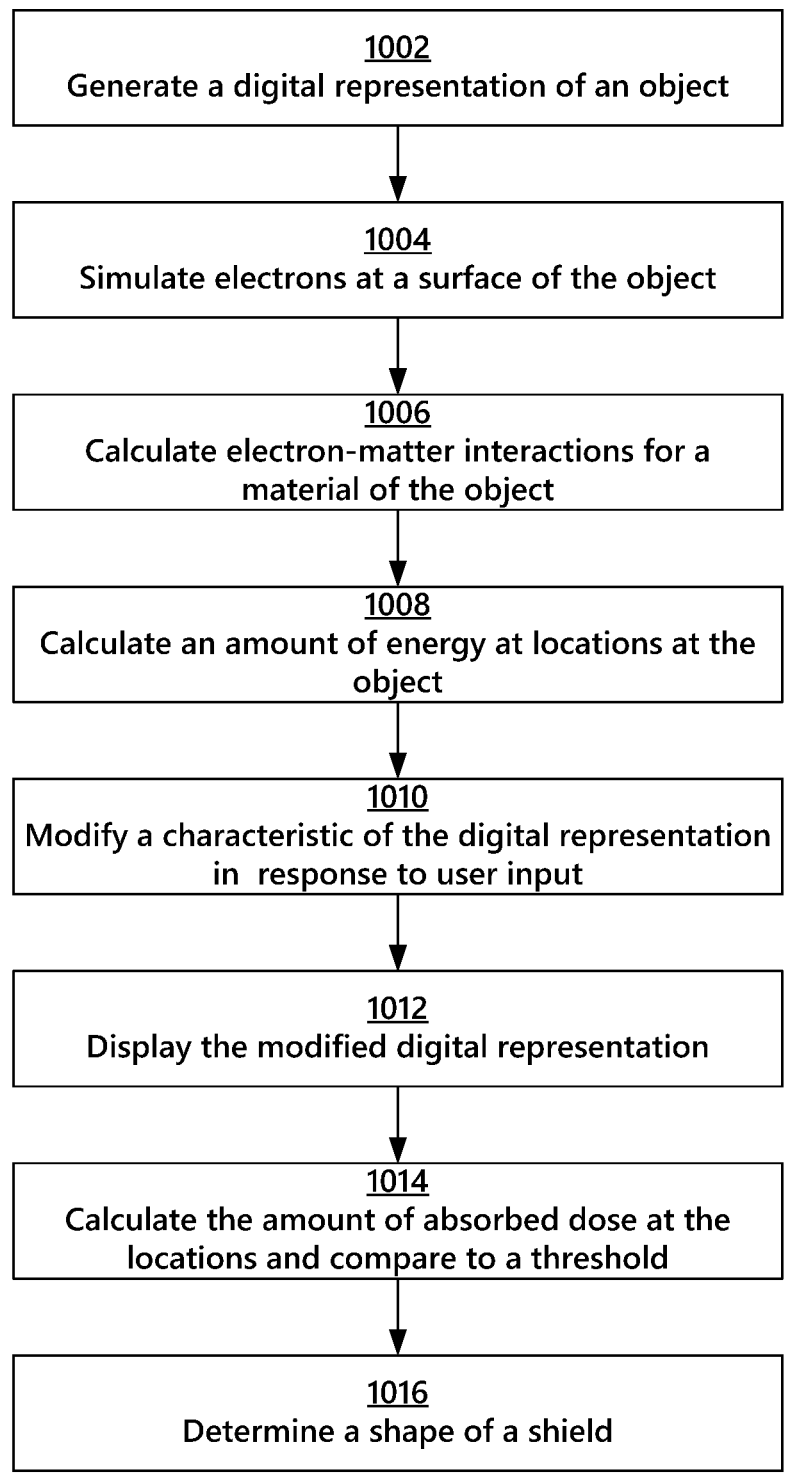
FIG. 10 is a flowchart of an example of a method for electron beam processing control in embodiments of the present invention.

FIG. 10 is a flowchart of a computer-implemented method for electron beam processing control in embodiments according to the present invention. All or some of the operations represented by the blocks in the flowchart can be implemented as computer-executable instructions residing on some form of non-transitory computer-readable storage medium (e.g., the memory 952) and executed by a computer system such as the computer system 900 of FIG. 9.

In block 1002, a digital representation of the object 101 is generated. The digital representation can be stored in memory of the computer system. The digital representation of the object includes a digital representation of components of the object, where each of the components is characterized by a respective single material. In embodiments, the digital representation of each component is a polyhedral surface mesh. In other embodiments, the digital representation of each component is a polygonal volume mesh.

In block 1004, a number of electrons are simulated at a surface of the object. In embodiments, energies, directions, and positions of incident electrons are calculated from a parameterized model of a source of the electron beam. In embodiments, simulated trajectories of individual particles are determined and may be displayed (e.g., on the output (display) device 956 of FIG. 9). In embodiments, parameters of the model are determined using a phantom.

In block 1006, electron-matter interactions for a material of the object are calculated.

In block 1008, an amount of energy deposited at respective locations at the object is calculated.

In block 1010, a characteristic of the digital representation of the object is modified in response to an input from a user (e.g., via the input device 954 of FIG. 9). The modification can include one or more of: changing a material of a component of the digital representation of the object; changing a position of the digital representation of the object relative to a source of the electron beam; changing an orientation of the digital representation of the object relative to a source of the electron beam; scaling a size of the object; removing a component from the digital representation of the object; and changing an attribute of a display of the digital representation of the object (e.g., the color and/or transparency of the components in the object can be changed, for visualization).

In block 1012, the modified digital representation of the object is displayed (e.g., on the output (display) device 956).

In block 1014, in embodiments, the amount of absorbed dose at each of the locations is calculated and compared against a dose threshold required to achieve adequate cross-linking of the materials. In embodiments, the amount of absorbed dose at each of the locations is compared against a dose threshold required to achieve adequate sterilization of the materials. In embodiments, the amount of absorbed dose at each of the locations is compared against a dose threshold required to avoid damaging the materials. The calculated amount of dose (e.g., absorbed dose) and/or the results of these comparisons can be displayed (e.g., on the output (display) device 956).

In block 1016, in embodiments, a shape of a shield (e.g., to protect selected components of the object against radiation from the electron beam) is determined.

The process parameters and sequence of steps described above are given by way of example only and can be varied as needed or desired. For example, while the steps illustrated and/or described above may be shown or discussed in a particular order, these steps do not necessarily need to be performed in the order illustrated or discussed. The various example methods described and/or illustrated herein may also omit one or more of the steps described herein or include additional steps in addition to those disclosed.

Although the subject matter has been described in language specific to structural features and/or methodological acts, it is to be understood that the subject matter defined in the disclosure is not necessarily limited to the specific features or acts described above. Rather, the specific features and acts described above are disclosed as example forms of implementing the disclosure.

Embodiments according to the invention are thus described. While the present disclosure has been described in particular embodiments, the invention should not be construed as limited by such embodiments, but rather construed according to the following claims.

What is claimed is:

1. A computer-implemented method for processing control of a beam of electrons, said method comprising:
   accessing a parameterized model of a source of said beam of electrons;
   generating a digital representation of a physical object, wherein said digital representation comprises a plurality of volume elements corresponding to volumes in said physical object;
   simulating a number of incident electrons at a surface of said physical object using said parameterized model;
   calculating a total amount of energy deposited in each volume element of said plurality of volume elements due to each interaction of each incident electron of said number of incident electrons with material in said each volume element;
   determining an amount of absorbed dose in said each volume element based on said total amount of energy deposited in said each volume element;
   displaying a three-dimensional distribution of said absorbed dose in said each volume element;
   comparing said amount of absorbed dose in said each volume element against a dose threshold required to achieve adequate sterilization of said material in said each volume element; and
   calculating values of parameters of said parameterized model based on results of the comparison of said amount of absorbed dose in said each volume element against said dose threshold.

2. The computer-implemented method of claim 1, wherein said physical object is composed of a plurality of components, wherein each component of said plurality of components is assigned a respective single material in said digital representation, and wherein each of said volumes in said physical object corresponds to a respective component of said plurality of components.

3. The computer-implemented method of claim 1, wherein said plurality of volume elements comprises a polyhedral surface mesh.

4. The computer-implemented method of claim 1, wherein said plurality of volume elements comprises a polygonal volume mesh.

5. The computer-implemented method of claim 1, further comprising:
   calculating a phase space of said each incident electron, wherein said phase space comprises an energy, direction, and position of said each incident electron, and wherein said phase space is calculated using said parameterized model of said source of said beam of electrons;
   using said phase space to identify a location where an interaction of said each incident electron and said material occurs; and
   using said location to identify a volume element of said plurality of volume elements.

6. The computer-implemented method of claim 5, further comprising:
   determining parameters of said parameterized model using a phantom having a plurality of designated locations for dosimeters.

7. The computer-implemented method of claim 1, further comprising modifying a characteristic of said digital representation in response to an input from a user, to generate a modified digital representation of said physical object, wherein said modifying comprises an operation selected from the group consisting of:
   changing said material to a different material;
   changing a position of said digital representation relative to said source of said beam of electrons;
   changing an orientation of said digital representation relative to said source of said beam of electrons;
   scaling a size of said physical object;
   removing a component from said digital representation; and
   changing an attribute of a display of said digital representation.

8. The computer-implemented method of claim 1, further comprising:
   determining a shape of a shield to protect selected components of said physical object against radiation from said beam of electrons.

9. A computer-implemented method for processing control of a beam of electrons, said method comprising:
   accessing a parameterized model of a source of said beam of electrons;
   generating a digital representation of a physical object, wherein said digital representation comprises a plurality of volume elements corresponding to volumes in said physical object;
   simulating a number of incident electrons at a surface of said physical object using said parameterized model;
   calculating a total amount of energy deposited in each volume element of said plurality of volume elements due to each interaction of each incident electron of said number of incident electrons with material in said each volume element;
   determining an amount of absorbed dose in said each volume element based on said total amount of energy deposited in said each volume element;
   displaying a three-dimensional distribution of said absorbed dose in said each volume element;
   comparing said amount of absorbed dose in said each volume element against a dose threshold required to avoid damaging said material in said each volume element; and
   calculating values of parameters of said parameterized model of said source based on results of the comparison of absorbed dose in said each volume element against said dose threshold.

10. The computer-implemented method of claim 9, wherein said physical object is composed of a plurality of components, wherein each component of said plurality of components is assigned a respective single material in said digital representation, and wherein each of said volumes in said physical object corresponds to a respective component of said plurality of components.

11. The computer-implemented method of claim 9, further comprising:
calculating a phase space of said each incident electron, wherein said phase space comprises an energy, direction, and position of said each incident electron, and wherein said phase space is calculated using said parameterized model of said source of said beam of electrons;
using said phase space to identify a location where an interaction of said each incident electron and said material occurs; and
using said location to identify a volume element of said plurality of volume elements.

12. A system for processing control of a beam of electrons, said system comprising:
memory that stores a digital representation of an object;
an input device coupled to said memory and operable for receiving input from a user;
a display device coupled to said memory; and
a processor coupled to said memory and operable for executing memory-resident components that, when executed, cause the system to:
access from said memory a parameterized model of a source of said beam of electrons;
generate a digital representation of a physical object, wherein said digital representation comprises a plurality of volume elements corresponding to volumes in said physical object;
simulate a number of incident electrons at a surface of said physical object using said parameterized model of said source of said beam of electrons;
calculate a total amount of energy deposited in each volume element of said plurality of volume elements due to each interaction of each electron of said number of incident electrons with material in said each volume element;
determine an amount of absorbed dose in said each volume element based on said total amount of energy deposited in said each volume element;
display a three-dimensional distribution of said absorbed dose within said each volume element;
compare said amount of absorbed dose in said each volume element against a dose threshold required to achieve adequate crosslinking of said material in said each volume element; and
calculate values of parameters of said parameterized model based on results of the comparison of said absorbed dose in said each volume element against said dose threshold.

13. The system of claim 12, wherein said memory-resident components, when executed, also cause said system to:
display a comparison of said amount of dose in said each volume element with at least one of a dose threshold and a dose range.

14. The system of claim 12, wherein said memory-resident components, when executed, also cause said system to display simulated trajectories of said each incident electron.

15. The system of claim 12, wherein said physical object is composed of a plurality of components, wherein each component of said plurality of components is assigned a respective single material in said digital representation, and wherein each of said volumes in said physical object corresponds to a respective component of said plurality of components.

16. The system of claim 12, wherein said plurality of volume elements comprises a polyhedral surface mesh.

17. The system of claim 12, wherein said plurality of volume elements comprises a polygonal volume mesh.

18. The system of claim 12, wherein said memory-resident components, when executed, also cause said system to:
calculate a phase space of said each incident electron, wherein said phase space comprises an energy, direction, and position of said each incident electron, and wherein said phase space is calculated using said parameterized model of said source of said beam of electrons;
using said phase space to identify a location where an interaction of said each incident electron and said material occurs; and
using said location to identify a volume element of said plurality of volume elements.

19. The system of claim 12, wherein said memory-resident components, when executed, also cause said system to perform an operation selected from the group consisting of:
change said material to a different material;
change a position of said digital representation relative to said source of said beam of electrons;
change an orientation of said digital representation relative to said source of said beam of electrons;
scale a size of said physical object;
remove a component from said digital representation; and
change an attribute of a display of said digital representation.

20. The system of claim 12, wherein said memory-resident components, when executed, also cause said system to determine a shape of a shield to protect selected components of said physical object against radiation from said beam of electrons.

* * * * *